United States Patent

Diel

[11] 3,985,745
[45] Oct. 12, 1976

[54] 3-IMINO-1,2,4-BENZOTRIAZINE-1-OXIDES
[75] Inventor: Peter J. Diel, Basel, Switzerland
[73] Assignee: Ciba-Geigy Corporation, Ardsley, N.Y.
[22] Filed: Mar. 11, 1975
[21] Appl. No.: 557,441

[30] Foreign Application Priority Data
  Mar. 15, 1974  Switzerland............... 3632/74
  Jan. 15, 1975  Switzerland............... 409/75

[52] U.S. Cl............................ 260/249.5; 424/249
[51] Int. Cl.²................................. C07D 253/08
[58] Field of Search............................ 260/249.5

[56] References Cited
UNITED STATES PATENTS
3,868,371   2/1975   Ley et al................. 260/249.5

Primary Examiner—John M. Ford
Attorney, Agent, or Firm—Harry Falber

[57] ABSTRACT

New 3-Imino-1,2,4-benzotriazine-1-oxides of formula I

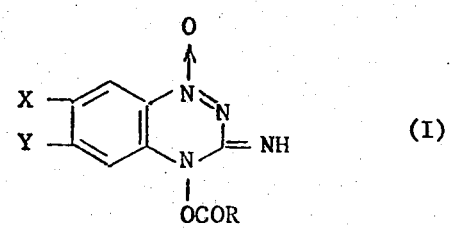

wherein

R represents an alkyl, alkenyl or haloalkyl radical, a phenyl or aralkyl radical optionally substituted by alkyl, alkoxy, haloalkyl, halogen or hydroxy, X and Y each independently represent hydrogen, halogen, an alkyl or alkoxy radical, or one of the two symbols represents a phenoxy or phenylsulphonyl radical optionally substituted by halogen, alkyl, haloalkyl and/or alkoxy which are active against harmful microorganisms are disclosed.

4 Claims, No Drawings

3-IMINO-1,2,4-BENZOTRIAZINE-1-OXIDES

The present invention relates to new microbicidally effective 1,2,4-benzotriazine oxides, to processes for producing these compounds, as well as to compositions containing them and to processes for the control of microorganisms by the use thereof.

The new 1,2,4-benzotriazine oxide derivatives correspond to formula I

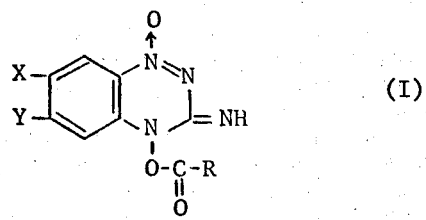

wherein
R represents an alkyl, alkenyl or haloalkyl radical, a phenyl or aralkyl radical optionally substituted by alkyl, alkoxy, haloalkyl, halogen or hydroxy,
X and Y each independently represent hydrogen, halogen, an alkyl or alkoxy radical, or one of the two symbols represents a phenoxy or phenylsulphonyl radical optionally substituted by halogen, alkyl, haloalkyl and/or alkoxy.

By alkyl radicals R in formula I are meant those having 1 to 18, preferably 1 to 6, carbon atoms in a straight chain; suitable such radicals are: methyl, ethyl, n-propyl, isopropyl, as well as the butyl, pentyl, hexyl, heptyl, octyl, nonyl, decyl, undecyl, dodecyl, tridecyl, tetradecyl, pentadecyl, hexadecyl, heptadecyl and octadecyl radicals which can be mono- or polysubstituted by methyl or ethyl. Preferred alkenyl radicals for R are those having 3 to 5 carbon atoms, such as, the propenyl, methylpropenyl or butenyl radicals; also suitable,, however, are ones having up to 18 carbon atoms in a straight chain, such as, e.g., a heptadecenyl radical. If R stands for an aralkyl radical, then suitable radicals are, in particular, the benzyl radical or a phenethyl or phenylpropyl radical, but also ones having a branched alkylene bridge. As a haloalkyl radical, R can represent an alkyl radical having 1 to 4 carbon atoms which is mono- or polysubstituted by bromine, chlorine, fluorine and iodine; e.g. the trifluoromethyl radical, β-haloethyl radical, etc.. Suitable for X and Y are mainly lower alkyl radicals having 1 to 5 carbon atoms in a straight chain. These form also the alkyl moiety of an alkoxy radical, such as, e.g., methoxy, ethoxy, n-propoxy or isopropoxy. Phenyl radicals, among which are meant also the phenoxy or phenylsulphonyl radical given under X or Y, as well as the aralkyl radicals mentioned for R, can carry up to 3 substituents identical or different with respect to each other, such as, e.g., the mentioned lower alkyl and alkoxy radicals, as haloalkyl radical the trifluoromethyl radical, as halogen preferably bromine, chlorine or fluorine. As substituent of 1,2,4-benzotriazine-1-oxide, halogen can be bromine, chlorine, fluorine or iodine.

The new 1,2,4-benzotriazine oxides of formula I are produced according to the present invention by reacting a 3-amino-1,2,4-benzotriazine-1,4-dioxide of formula II

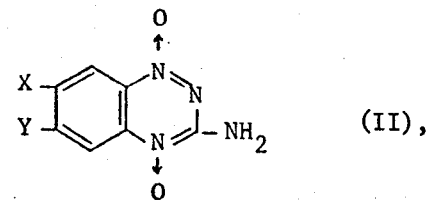

in the presence of a solvent or diluent, either with a carboxylic acid halide of formula III

wherein R has the meanings given under formula I, in the presence of an acid-binding agent, or with an open-chain or branched-chain carboxylic acid anhydride corresponding to the meanings of R.

Suitable solvents and/or diluents for the reactions are substances that are inert to the reactants, such as aromatic hydrocarbons, e.g. benzene, toluene or xylenes; halogenated hydrocarbons such as chlorobenzene, chloroform, or carbon tetrachloride; ethers and ethereal compounds such as dialkyl ether, and cyclic ethers such as dioxane; ketones such as acetone or methyl ethyl ketone; and mixtures of such solvents with each other or with water (two-phase systems), particularly the mixture methyl ethyl ketone/water.

Preferred acid-binding agents are inorganic bases such as, e.g., the hydroxides of alkali metals and alkaline-earth metals. It is also possible, however, to use organic bases such as tertiary amines, e.g. pyridine and pyridine bases, or trialkylamines such as triethylamine.

Preferred carboxylic acid halides are the chlorides and bromides. In the case of the anhydrides used for the reaction, these are anhydrides of monocarboxylic acids; the following are, for instance, suitable: acetanhydride, propionic acid anhydride or butyric acid anhydride, as well as the anhydrides of the corresponding halogenated alkanecarboxylic acids.

The starting materials of formula II are known, and are produced by the processes described by Arndt and Eistert in Chem. Ber. 46 (1913) 3522, Robinson and Schofield in J. Chem. Soc. 1957, 3186-94 and Ley and Seng in Angew. Chem. 84, 21 (1972).

The following examples serve to illustrate the process of the invention.

EXAMPLE 1

3-Imino-4-acetoxy-1,2,4-benzotriazine-1-oxide 17.8 g of 3-amino-1,2,4-benzotriazine-1,4-di-N-oxide is dissolved in 200 ml of glacial acetic acid at 80° C. To the solution there is added dropwise 15.3 g of acetic acid anhydride, and stirring is then maintained for 3 hours at 90° C. The mixture is cooled to 15° C; the yellow precipitate is filtered off under suction, washed with water and dried in vacuo. Yield: 13 g, M.P.: 194°–196° C.

EXAMPLE 2

3-Imino-4-benzoyloxy-1,2,4-benzotriazine-1-oxide 13.5 g of 3-amino-1,2,4-benzotriazine-1,4-di-N-oxide and 45.2 g of benzenecarboxylic acid anhydride are dissolved at room temperature in 75 ml of trifluoroacetic acid, and the solution is subsequently stirred for 3 hours at 70° C. The solution is allowed to cool to room temperature; it is then poured into 200 ml of water and the yellow solid substance is filtered off with suction. The residue is stirred in 25 ml of glacial acetic acid at 45° C, filtered off with suction and washed with water. Drying is carried out in vacuo. M.P.: 177°–179° C.

EXAMPLE 3

3-Imino-4-(3',4',5'-trimethoxy)-benzoyloxy-7-methoxy-1-2,4-benzotriazine-1-oxide 20.8 g of 3-amino-7-methoxy-1,2,4-benzotriazine-1,4-di-N-oxide is placed into 400 ml of dioxane at room temperature. There are then added portionwise 8 g of pyridine and subsequently 34.5 g of 3,4,5-trimethoxybenzoyl chloride; the temperature increases from 20° C to 30° C. The whole is stirred for 24 hours at 50° C; it is then allowed to cool to room temperature and filtration under suction is performed. The residue is stirred up in 400 ml of cold water, filtered off with suction, dried, and recrystallised from 900 ml of methylcellosolve; M.P.: 206°–208° C.

EXAMPLE 4

3-Imino-4-phenylacetoxy-1,2,4-benzotriazine-1-oxide 17.8 g of 3-amino-1,2,4-benzotriazine-1,4-di-N-oxide is dissolved in 250 ml of water and 4 g of sodium hydroxide, and the solution is filtered into a sulphonating flask. The solution is cooled to 0° C. There is then added dropwise in the course of 20 minutes a mixture of 27.6 g of phenylacetyl chloride and 40 ml of methyl ethyl ketone, whereupon there forms an oily precipitate. After completion of the dropwise addition, 60 ml of ethanol is added and stirring is maintained overnight. The crystalline precipitate is filtered off under suction, washed with alcohol and dried. Yield: 9 g; M.P.: 165°–167° C.

The following compounds were produced by processes analogous to those described in the preceding examples:

3-imino-4-propionyloxy-7-methoxy-1,2,4-benzotriazine-1-oxide; M.P.: 181°–183° C;

3-imino-4-caprylyloxy-7-methoxy-1,2,4-benzotriazine-1-oxide; M.P.: 170° C, decomposition;

3-imino-4-crotonyloxy-7-methyl-1,2,4-benzotriazine-1-oxide; M.P.: 202°–204° C;

3-imino-4-acetoxy-7-methyl-1,2,4-benzotriazine-1-oxide; M.P.: 196°–197° C;

3-imino-4-(4'-chlorobenzoyloxy)-1,2,4-benzotriazine-1-oxide; M.P.: 168°–171° C;

3-imino-4-(2',4'-dichlorobenzoyloxy)-1,2,4-benzotriazine-1-oxide; M.P.: 210°–214° C;

3-imino-4-(4'-methylbenzoyloxy)-1,2,4-benzotriazine-1-oxide; M.P.: 158°–161° C;

3-imino-4-lauroyloxy-1,2,4-benzotriazine-1-oxide; M.P.: 164°–168° C;

3-imino-4-(3'-trifluoromethylbenzoyloxy-1,2,4-benzotriazine-1-oxide; M.P.: 173°–176° C;

3-imino-4-acetoxy-7-phenoxy-1,2,4-benzotriazine-1-oxide; M.P.: 177°–180° C;

3-imino-4-acetoxy-6-phenylsulphonyl-1,2,4-benzotriazine-1-oxide; M.P.: 207°–209° C;

3-imino-4-chloroacetoxy-1,2,4-benzotriazine-1-oxide; M.P.: 142°–144° C.

The new 1,2,4-benzotriazine oxides of formula I are characterised by a good antimicrobial action, and can accordingly be used to wide extent for the control of microorganisms. To be emphasised is a good inhibitory and destroying action against gram-positive and gram-negative bacteria, as well as against fungi; furthermore, the new compounds are very effective against germs pathogenic for animals. They are suitable, in particular, for the controlling of respiratory diseases (CRD) in poultry caused by E. coli airsacculitis.

The compounds of the present invention exhibit also an excellent growth-promoting action in the case of animals of commercial value, e.g. pigs, poultry and also ruminants such as cattle or sheep.

In the rearing of animals of commercial value, such as pigs, poultry and ruminants, e.g. cattle, calves and sheep, it is desirable for economic reasons to achieve in the shortest possible time, and with the smallest possible expenditure on feeding stuffs, a maximum yield of meat or of milk and eggs. In order to obtain this, it is suggested according to the invention to use the compounds of formula I as supplementary feed for animals of commercial value.

The active substances of formula I according to the invention are added, either direct or in the form of a premix, to the feed or into the drinking troughs for the mentioned animals in amounts of 1 to 500 ppm relative to the total feed or total drinking liquid.

Suitable premixes consist, e.g., of a mixture of the active substance with kaolin, limestone, aluminium oxide, ground mussel shells, bolus alba, aerosil, starch or lactose. A feed mixture is prepared by thoroughly mixing the required amount of premix with the appropriate amount of a commercial standard feed.

By virtue of their wide microbicidal range of action, the compounds of the present invention can also be used — as mentioned — in veterinary medicine for the control of pathogenic microorganisms on and in the animal, particularly on the skin and in the intestinal tract and urogenital system. For the control of pathogenic microorganisms in veterinary medicine and/or for the obtainment of a growth-promoting action in the case of animals of commercial value, the compounds of the present invention can be combined with the following substances:

1. Antibiotics

Penicillin and derivatives thereof,
Cephalosporin and derivatives thereof,
Chloramphenicol,
Tetracyclines (e.g. chlorotetracycline, oxytetracycline),
Rifamycin and derivatives thereof (e.g. Rifampin),
Linocomycin,
Bacitracin and salts thereof,
Pyrrolnitrin,
Myxin,
Streptomycin,
Nigericin,
Parvulin,
Spiramycin,
Thiopeptin,
Tylosin.

2. Sulphonamides

N'-(3,4-dimethyl-5-isoxazolyl)-sulphanilamide,
N'-2-pyrazinylsulphanilamide,
2,4-dimethoxy-6-sulphamylamido-1,3-diazine,
N'-(4-methyl-2-pyrimidyl)-sulphanilamide.

3. Nitrofurans 3-(5-nitrofurfurylideneamino)-2-oxazolidinone,
5-morpholinomethyl-3-(5-nitrofurfurylideneamino)-2-oxazolidinone, 3-amino-6-[2-(nitro-2-furyl)vinyl]-pyridazine,
1,5-di-(5'-nitro-2'-furyl)-penta-1,4-dien-one-(3)-2''-amidinohydrazone-hydrochloride.

4. Diaminopyrimidines 2,4-diamino-5-(3,4,5-trimethoxybenzyl)-pyrimidine,
2,4-diamino-5-(3,4-dimethoxybenzyl)-pyrimidine,
2,4-diamino-5-(p-chlorophenyl)-6-ethylpyrimidine.

5. Hydroxyquinolines 5,7-dichloro-8-hydroxyquinaldine,
5-chloro-7-iodo-8-hydroxyquinoline.

6. Hydroxyquinolinecarboxylic acids and hydroxynaphthyridine acids 1-ethyl-1,4-dihydro-7-methyl-4-oxo-1,8-naphthyridine-3-carboxylic acid, oxolinic acid.

7. Quinoxaline-di-N-oxides quinoxaline-1,4-di-N-oxide,
3-(1,4-dioxo-2-quinoxalinemethylene)-carbazinic acid methyl ester.

8. Halogenated hydroxydiphenyl ethers 2-hydroxy-2'4,4'-trichloro-diphenyl ether.

9. Nitrohydroxydiphenyl ethers

10. Optionally halogenated salicylic anilides

11. Triarylmethylimidazoles di-(phenyl)-2-chlorophenyl-imidazolyl(1)-methane.

12. Vitamins 13. 3-Hydroxy-2-methyl-4-pyrone 14. 2-Mercaptoimidazole

15. Ethoxylated alcohols such as R—O(CHCH$_2$O)$_n$H.

16. 2-Bromo-5-nitrothiazole.

17. Guanidines

18. N-Substituted aminoacetic acids

19. β-Nitropropionic acid

20. Phenylcyclopropylamine 21. 2-(4-Thiazolyl)-benzimidazole

22. Piperazine and salts thereof

23. Benzodiazepinone derivatives

24. Dihydroxydiphenylsulphides 25. 4,5-Dihydroxy-2,4,6-octatrienedicarboxylic acids 26. 2-Formyl-4-chlorophenoxyacetic acids 27. Straight-chain aliphatic alcohols 28. 2-Chloro-10-(3-dimethylaminopropyl)-phenothiazine 29. Acetoxybenzoic acid 30. Auxins:

3,5-di-sec.butyl-α,β,δ-hydroxy-β-oxo-1-cyclopentene-valeric acid,
3,4-di-sec.butyl-δ-hydroxy-β-oxo-1-cyclopentene-valeric acid.

The microbicidal action against microorganisms pathogenic for poultry is determined by means of the following tests:

Foul reared in an isolated state are fed with a basic diet free from Coccidiostatica and antibiotics. The infection is effected with a standardised suspension of an Escherichia coli strain pathogenic for fowl in a brain-heart infusion directly into the posterior thoracal laryngocele. The fowl are simultaneously treated with an active-substance suspension in physiological saline solution with the addition of 1% of Tween 80.

A group of 10 fowl is used for each active substance. A control is provided by fowl
 a. not infected and not treated, and
 b. infected but untreated.

The results of the test are evaluated after 7 days. The surviving fowl are dissected. The evaluation is made on the basis of mortality and on the lesions of the laryngocele ascertainable on dissection. The spread of lesions extending beyond the local reaction at the point of inoculation is expressed in percentages.

| Active substance | Treatment with 100 mg/kg of active substance | | Untreated control fowl | | | |
|---|---|---|---|---|---|---|
| | Mortality % | Lesions % | Mortality not infect. | infect. | Lesions not infect. | infect. |
| 3-Imino-4-benzoyloxy-1,2,4-benzotriazine-1-oxide | 0 | 10 | 0 | 50 | 0 | 100 |
| 3-Imino-4-acetoxy-1,2,4-benzotriazine-1-oxide | 0 | 20 | 0 | 80 | 0 | 100 |
| 3-Imino-4-propionyl-oxy-7-methoxy-1,2,4-benzotriazine-1-oxide | 0 | 20 | 0 | 60 | 0 | 100 |

Determination of the minimum inhibiting concentrations (MIC) against bacteria and fungi Stock solutions (1.5%) of the compounds of formula I in methylcellosolve are prepared, and these subsequently diluted so that the incorporation of 0.3 ml of the stock solution in each case and of each dilution in 15 ml each time of warm nutrient-agar produces a concentration series of 300, 100, 30, 10, 3, 1, and so forth, ppm of active substance in the agar. The mixtures whilst still warm are poured into dishes and, after solidification, inoculated with the following test organisms:

Gram-positive bacteria

Staphylococcus aureus,
Sarcina ureae,
Streptoococcus faecalis,
Streptococcus agalactiae,
Corynebacterium diphteroides,
Bacillus subtilis,
Mycobacterium phlei.

Gram-negative bacteria

Escherichia coli,
Salmonella pullorum,
Salmonella cholerae-suis,
Bordetella bronchiseptica,
Pasteurella multocida,
Proteus vulgaris.
Proteus rettgeri,
Pseudomonas fluorescens,
Pseudomonas aeroginosa.

Fungi

Trichophyton gypseum,
Trichophyton gallinae,
Trichophyton verrucosum,
Candida albicans,
Candida krusci,
Aspergillus niger,
Aspergillus flavus,
Penicillium funiculosum,
Penicillium expansum,
Trichoderma viride,
Fusarium oxysporum,
Chaetonium globosum,
Alternaria tenuis,
Paecilomyces varioti,
Stachybotrys atra.

After an incubation of 48 hours at 37° C (bacteria) and 5 days at 28° C (fungi), the minimum concentration (ppm) of the active substances with which the growth of the test organisms is inhibited is determined. The recorded values for the minimum inhibiting concentration (MIC) in the case of compounds of formula I are clearly below the starting concentration of 300 ppm.

Determination of the microbicidal action

A. In order to determine whether the active substances had destroyed the test germs (biocidal effect) or had merely inhibited them in their growth (biostatic effect), sterile filter paper disks of 20 mm diameter are placed on the inoculation sites of the germs exhibiting no growth, and, after a contact time of 30 minutes, the germs transferred by means of these disks to sterile agar blocked with respect to the active substances with Tween 80. The contact time is again 30 minutes. If no growth of the transferred germs on the secondary agar-dish is observed, the germs will have been destroyed by the active substance in the first dish, i.e. the active substance in the concentrations concerned has a biocidal action on the germs examined.

The following additional test is carried out for confirmation of the preceding finding:

B. Active substances of formula I are used to prepare the following solutions:
5% of active substance,
5% of Na-N-cocos-β-aminopropionate,
20% of permutite water,
70% of ethylcellosolve (ethylene glycol monoethyl ether).

Aliquot parts of these solutions are converted with sterile distilled water into emulsions of 1000 ppm, 500 ppm, 250 ppm and 125 ppm active-substance content. Samples of 9.9 ml of the emulsions are inoculated with 0.1 ml of germ suspensions (ca. $10^7$ germs/ml).

Test organisms

Staphylococcus aureus,
Strephylococcus faecalis
Bacillus subtilis,
Proteus vulgaris.

After an action time of one minute, a specimen of the inoculated emulsions is placed in each case into 10 ml of sterile brain-heart-infusion-broth; after an incubation time of 24 hours at 37°, the brain-heart-infusion-broth is examined for cloudiness (germ growth).

The examined compounds of formula I exhibited in the above tests a biocidal action.

The following compositions, for example, are suitable as feed additives:

For the preparation in each case of 6 kg of final feed containing (a) 25 ppm, (b) 50 ppm, (c) 200 ppm and (d) 400 ppm of active substance, the following feed mixtures are used:

| | | |
|---|---|---|
| a) | 0.15 part by weight | of one of the compounds of formula I, |
| | 49.85 parts by weight | of bolus alba, |
| | 150.0 parts by weight | of standard feed for poultry, pigs or ruminants; |
| b) | 0.30 part by weight | of one of the compounds of formula I, |
| | 49.70 parts by weight | of bolus alba, |
| | 5.0 parts of silicic | acid, |
| | 150.0 parts by weight | of standard feed for poultry, pigs or ruminants; |
| c) | 1.2 parts by weight | of one of the compounds of formula I, |
| | 43.8 parts by weight | of bolus alba, |
| | 5.0 parts by weight | of silicic acid, |
| | 150.0 parts by weight | of standard feed for poultry, pigs or ruminants; |
| d) | 2.4 parts by weight | of one of the compounds of formula I, |
| | 47.6 parts by weight | of bolus alba, |
| | 150.0 parts by weight | of standard feed for poultry pigs or ruminants. |

The supplementary feed according to the invention is either added direct to the carriers or absorbed, e.g. dissolved in chloroform, onto the carriers. The material is subsequently ground to obtain the desired particle size of, e.g., 5 to 10 microns. These feed premixes are worked up with 5800 parts by weight of finished drinking liquid. Furthermore, the feed premixes can be tabletted to give 6000 parts by weight of standard feed (feed pellets).

Compared with the control animals fed with corresponding feed mixtures and forms not containing active substance, the animals fed with the above-mentioned feed mixtures clearly show the growth-promoting action of the new compounds.

I claim:
1. A 3-Imino-1,2,4-benzotriazine-1-oxide of formula I

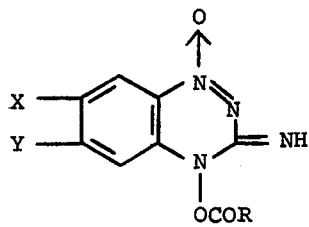

wherein

R represents $C_1$–$C_{18}$ alkyl, $C_3$–$C_{18}$ alkenyl or $C_1$–$C_4$ haloalkyl, phenyl benzyl, phenethyl or phenylpropyl optionally substituted by $C_1$–$C_5$ alkyl, $C_1$–$C_5$ alkoxy, trifluoromethyl, halogen or hydroxy, X and Y each independently represent hydrogen, halogen, $C_1$–$C_5$ alkyl or $C_1$–$C_5$ alkoxy, or one of the two symbols represents a phenoxy or phenylsulphonyl radical optionally substituted by halogen, $C_1$–$C_5$ alkyl, trifluoromethyl or $C_1$–$C_5$ alkoxy.

2. 3-imino-4-benzoyloxy-1,2,4-benzotriazine-1-oxide according to claim 1.

3. 3-imino-4-acetoxy-1,2,4-benzotriazine-1-oxide according to claim 1.

4. 3-imino-4-propionyloxy-7-methoxy-1,2,4-benzotriazine-1-oxide according to claim 1.

* * * * *